(12) United States Patent
Hirayama et al.

(10) Patent No.: US 6,884,365 B1
(45) Date of Patent: Apr. 26, 2005

(54) GAS FOR PLASMA REACTION AND METHOD FOR PRODUCTION THEREOF

(75) Inventors: Toshinobu Hirayama, Kawasaki (JP); Toshiro Yamada, Kawasaki (JP); Tatsuya Sugimoto, Kawasaki (JP); Mitsuru Sugawara, Kawasaki (JP)

(73) Assignee: Zeon Corporation, Tokyo (JP)

( * ) Notice: Subject to any disclaimer, the term of this patent is extended or adjusted under 35 U.S.C. 154(b) by 0 days.

(21) Appl. No.: 09/979,508

(22) PCT Filed: May 24, 2000

(86) PCT No.: PCT/JP00/03308

§ 371 (c)(1),
(2), (4) Date: Nov. 23, 2001

(87) PCT Pub. No.: WO00/71497

PCT Pub. Date: Nov. 30, 2000

(30) Foreign Application Priority Data

May 24, 1999 (JP) ............................................ 11-143562

(51) Int. Cl.$^7$ ........................ C09K 13/00; C09K 13/06; H01L 21/3065
(52) U.S. Cl. ...................... 252/79.1; 252/79.4; 438/706
(58) Field of Search .............................. 252/79.1, 79.4, 252/79.2; 438/706

(56) References Cited

U.S. PATENT DOCUMENTS 6,159,862 A * 12/2000 Yamada et al. ............. 438/712
6,465,359 B1 * 10/2002 Yamada et al. ............. 438/706

OTHER PUBLICATIONS

Google Search. Air Liquide Electronics, High Purity Specialty Gases and Chemicals for the Semiconductor Industry OCTAFLUOROCYLOPENTENE C5F8 Perfluorocyclopentene, Aug. 2002, 2 pages.*

Google Search. PRAXAIR. OCTAFLUOROCYCLOPENTENE—(C5F8), Aug. 2003, 2 pages.*

* cited by examiner

*Primary Examiner*—Nadine G. Norton
*Assistant Examiner*—Lynette T. Umez-Eronini
(74) *Attorney, Agent, or Firm*—Armstrong, Kratz, Quintos, Hanson & Brooks, LLP

(57) ABSTRACT

A high-purity gas for plasma reaction having an octafluorocyclopentene purity of at least 99.9% by volume based on the total volume of the gas for plasma reaction, wherein the total content of nitrogen gas and oxygen gas, contained as trace gaseous ingredients of the remainder, is not larger than 200 ppm by volume. This high-purity gas for plasma reaction can be produced by (1) a process of distilling crude octafluorocyclopentene in an inert gas of group 0, or (2) a process of distilling crude octafluorocyclopentene into a purity of at least 99.9% by volume, and then, removing an impurity remainder.

6 Claims, No Drawings

GAS FOR PLASMA REACTION AND METHOD FOR PRODUCTION THEREOF

TECHNICAL FIELD

This invention relates to a gas for plasma reaction used, for example, for the production of a semiconductor device. More particularly, it relates to a gas for plasma reaction, comprised of high-purity octafluorocyclopentene, and an improved process for producing the gas for plasma reaction.

BACKGROUND ART

With the advance in high integration and high performance of semiconductor devices such as VLSI (Very Large Scale Integrated Circuit) and ULSI (Ultra Large Scale Integrated Circuit), technical demands for a gas for plasma reaction used in the production process of these semiconductor devices are becoming increasingly strict. Thus, a uniform and high-purity gas for plasma reaction is eagerly desired.

As a gas for plasma etching, saturated fluorocarbon gases such as tetrafluorocarbon gas have heretofore been widely used. However, it is said that saturated fluorocarbon gases have a long life in the air, i.e., a life of several-thousand years or more, and exert a considerable influence upon the global warming. From a viewpoint of prevention of global warming, various fluorine-containing compounds have been developed as alternatives for saturated fluorocarbon gases. Especially octafluorocyclopentene ($C_5F_8$), which has an unsaturated bond and a very short life in the air, attracts attention as a favorable gas for plasma reaction for use in the production of various semiconductor devices.

However, for example, when a crude octafluorocyclopentene product, which is prepared by allowing 1,2-dichlorohexafluorocyclopentene to react with potassium fluoride, is subjected to fractional distillation by a conventional industrial method to give distilled octafluorocyclopentene, and the distilled octafluorocyclopentene is used for dry etching a silicon compound layer such as a silicon oxide layer, satisfactory etching rate and selectivity to a protective film such as polysilicon film and photoresist film are difficult to obtain. Further, it is also difficult to conduct etching at a high rate and uniformly.

DISCLOSURE OF THE INVENTION

In view of the foregoing problems of the prior art, an object of the present invention is to provide a gas for plasma reaction exhibiting a high selectivity to a material to be etched and a high etching rate, and a further object is to provide a process for producing the gas for plasma reaction.

To achieve the above-mentioned object, the present inventors made extensive research as to the influence of octafluorocyclopentene, especially impurities contained in octafluorocyclopentene, upon the performance of plasma reaction, and found that certain impurities greatly influence the performance of plasma reaction. A process for obtaining octafluorocyclopentene with an ultra-high purity by efficiently removing certain impurities influencing the performance of plasma reaction could be found. Based on these findings, the present invention has been completed.

Thus, in accordance with the present invention, there are provided:

(1) a gas for plasma reaction comprised of octafluorocyclopentene, characterized in that the gas for plasma reaction has an octafluorocyclopentene purity of at least 99.9% by volume based on the total volume of the gas for plasma reaction; and the total content of nitrogen gas and oxygen gas, contained as trace gaseous ingredients of the remainder, is not larger than 200 ppm by volume;

(2) the gas for plasma reaction as mentioned above in (1), which has a moisture content of not larger than 20 ppm by weight; and (3) the gas for plasma reaction as mentioned above in (1) or (2), which is used for dry etching, chemical vapor deposition or ashing.

In accordance with the present invention, there are further provided:

(4) a process for producing a gas for plasma reaction mentioned above in (1) or (2), characterized by distilling a crude reaction product predominantly comprised of octafluorocyclopentene in an inert gas of group 0;

(5) a process for producing a gas for plasma reaction mentioned above in (1) or (2), characterized by comprising a first step of distilling a crude reaction product predominantly comprised of octafluorocyclopentene into a purity of at least 99.9% by volume, and a second step of removing trace amounts of impurities of the remainder;

(6) the process for producing a gas for plasma reaction as mentioned above in (5), characterized in that, in the second step, a distilled product obtained in the first step is refluxed with heating in an inert gas of 0 group;

(7) the process for producing a gas for plasma reaction as mentioned above in (5), characterized in that, in the second step, a distilled product obtained in the first step is subjected to simple distillation in an inert gas of 0 group;

(8) the process for producing a gas for plasma reaction as mentioned above in (5), characterized in that, in the second step, a distilled product obtained in the first step is subjected to degassing under a reduced pressure at a low temperature;

(9) the process for producing a gas for plasma reaction as mentioned above in (5), characterized in that, in the second step, the distilled product treated by the process (6), (7) or (8), mentioned above, is further placed in contact with a molecular sieve or an adsorbent; and

(10) the process for producing a gas for plasma reaction as mentioned above in (4), (6) or (7), wherein the inert gas of group 0 is at least one inert gas selected from helium gas, neon gas and argon gas.

In accordance with the present invention, there is further provided:

(11) a process for producing a semiconductor device which comprises at least one step selected from a dry etching step, a chemical vapor deposition step and an ashing step; in each step, the gas for plasma reaction mentioned above in (1) being used.

BEST MODE FOR CARRYING OUT THE INVENTION

Plasma Reaction Gas

A gas for plasma reaction of the present invention has an octafluorocyclopentene purity of at least 99.9% by volume based on the total volume of the gas for plasma reaction as an indispensable feature; and is further characterized in that the total content of nitrogen gas and oxygen gas, contained as trace gaseous ingredients of the remainder, is not larger than 200 ppm by volume.

The purity of octafluorocyclopentene is preferably at least 99.95% by volume and more preferably at least 99.98% by volume, based on the total volume of the gas for plasma reaction. The total content of nitrogen gas and oxygen gas is preferably not larger than 150 ppm by volume and more preferably not larger than 100 ppm by volume. Further, in addition to the above-mentioned features, the moisture content is preferably not larger than 200 ppm by weight for more advantageously achieving the object of the present invention.

By the term "gas for plasma reaction" is used herein is meant a gas which is produced by the specific process for production of a gas for plasma reaction according to the present invention, explained below, or by other production processes, and which is used for plasma reaction in a state of being filled in an appropriate vessel, for example, for the production of a semiconductor device. The gas for plasma reaction of the present invention may be filled in an appropriate vessel as a mixed gas thereof with another gas for plasma reaction or with a diluent gas, provided that the object of the present invention can be achieved. Further, a gas for plasma reaction of the present invention once filled in an appropriate vessel can be taken therefrom, and then filled in an another vessel as a mixed gas thereof with another gas for plasma reaction or with a diluent gas, provided that the object of the present invention can be achieved.

By the term "octafluorocyclopentene purity" as used herein, we mean a purity as expressed in % by volume which is calculated from the value in % by weight as determined by gas chromatography analysis (hereinafter abbreviated to "GC analysis") according to the internal standard substance method. The total content of nitrogen gas and oxygen gas means the total of a content in ppm by volume of nitrogen gas and a content in ppm by volume of oxygen gas, both of which are measured by GC analysis. The value in ppm by volume can be said a value in ppm by mol. The moisture content usually means a content of moisture in ppm by weight as measured by the Karl-Fischer method.

Octafluorocyclopentene constituting a gas for plasma reaction of the present invention is a known substance having a boiling point of 27° C. at normal pressure, and can be produced by known processes.

As a typical example of the production processes, the present inventors have proposed in Japanese Unexamined Patent Publication No. H9-95458 a process for allowing 1,2-dichlorohexafluorocyclopentene to react with potassium fluoride in dimethylformamide (DMF) in a stream of nitrogen, and, while the reaction is continued, withdrawing the reaction product from a distillation apparatus equipped in a reactor. Thus, octafluorocyclopentene having a purity of 99.8% to 99.98% can be obtained (see Examples 1 and 2 in the specification of the patent publication). It is described in the patent publication that this octafluorocyclopentene is useful as a raw material for medicines, pesticides, liquid crystals and polymers.

The present inventors have found that, when octafluorocyclopentene is treated in a liquefied state at a temperature below the boiling point, i.e., below 27° C., in the above-mentioned production process, air (that is, nitrogen gas and oxygen gas) and nitrogen gas within a production equipment are very rapidly dissolved in octafluorocyclopentene upon contact therewith. For example, the total content of nitrogen gas and oxygen gas, dissolved in liquefied octafluorocyclopentene, reaches a value in the range of 500 ppm to 700 ppm at a temperature of 20° C., and occasionally reaches several thousand ppm at a temperature of −20° C. Even if the dissolved gas ingredients are once removed, when octafluorocyclopentene is stored in a nitrogen gas atmosphere or in the air, nitrogen gas and oxygen gas are rapidly dissolved therein whereby octafluorocyclopentene having gas ingredients dissolved therein is restored.

The present inventors have found further that, when liquid octafluorocyclopentene is filled in a bomb and then the octafluorocyclopentene is taken out in a gas state from the bomb, nitrogen gas and oxygen gas, dissolved in the liquid octafluorocyclopentene, are concentrated in a gasified octafluorocyclopentene. Thus, the contents of nitrogen gas and oxygen gas greatly vary with time in the course of taking octafluorocyclopentene.

In the case where moisture having a boiling point higher than that of octafluorocyclopentene, and organic ingredients other than octafluorocyclopentene are contained, as octafluorocyclopentene gas is drawn from a bomb, the contents of these ingredients in liquid octafluorocyclopentene increase.

By the "organic ingredients other than octafluorocyclopentene" as herein used, we mean very minor amounts of ingredients such as raw materials accompanying octafluorocyclopentenes, and intermediates and by-products which are produced in the course of production of octafluorocyclopentene. As specific examples of the organic ingredients, there can be mentioned 1,2-dichlorohexafluorocyclopentene, 1-chloroheptafluorocyclopentene, chlorononafluorocyclopentane, perfluorocyclopentadiene, perfluorobutadiene, perfluorocyclobutene and perfluorocyclopentane.

When octafluorocyclopentene produced by the conventional processes as mentioned above is used as a gas for plasma reaction in a dry etching step for making a semiconductor device, a high selectivity to a material to be etched and a high etching rate cannot be obtained for the following reasons.

First, impurities such as nitrogen gas, oxygen gas, moisture and the above recited chlorine-containing compounds are dissipated to produce various radicals, i.e., etching species, giving a baneful influence upon a plasma reaction.

Secondly, when the content of nitrogen gas exceeds a certain level, a plasma reaction of octafluorocyclopentene is shifted from decomposition of radicals to polymerization thereof, thus producing a polymer deposit.

Thirdly, when octafluorocyclopentene is taken out from a vessel, the amounts of volatilized nitrogen gas, oxygen gas, moisture and the above-recited chlorine-containing compounds greatly vary with time. Therefore, it is difficult to stably conduct a plasma reaction under constant conditions.

In contrast, a gas for plasma reaction of the present invention is characterized as having an octafluorocyclopentene purity of at least 99.9% by volume based on the total volume of the gas for plasma reaction, and further characterized in that the total content of nitrogen gas and oxygen gas, contained as trace gaseous ingredients of the remainder, is not larger than 200 ppm by volume. Due to these features, the gas for plasma reaction of the present invention does not cause any disadvantage of the above-mentioned three reasons, and enables to attain the object of the present invention.

When a gas for plasma reaction of the present invention characterized as having the above-mentioned features has a moisture content of not larger than 20 ppm by weight, the object of the present invention can be attained more definitely.

Use of Gas for Plasma Reaction

A gas for plasma reaction of the present invention is especially suitable for a plasma reaction involved in dry etching, chemical vapor deposition (hereinafter abbreviated to "CVD") or ashing, but its use is not limited thereto.

(1) Dry Etching

The dry etching using a gas for plasma reaction of the present invention is directed to etch a substrate to form a highly integrated minute pattern thereon, for example, in the step of making a semiconductor device. The substrate to be etched includes, for example, a glass substrate, a silicon single crystal wafer and a gallium-arsenic substrate, which have a surface film layer composed of a material to be etched away.

As specific examples of the material to be etched, there can be mentioned silicon oxide, silicon nitride, aluminum, tungsten, molybdenum, tantalum, titanium, chromium, chromium oxide and gold. A suitable example of the substrate to be etched is a silicon layer having a silicon oxide or aluminum film layer. When the material to be etched is silicon oxide, a layer of a photoresist or polysilicon is preferably formed on the silicon oxide as a protective film layer.

In the dry etching using a gas for plasma reaction of the present invention, plasma having a high density of at least $10^{10}$ ions/cm$^3$ is generated. A plasma density in the range of about $10^{10}$ to $10^{13}$ ions/cm$^3$ is preferable for manifesting the maximum performance of plasma and forming a minute pattern. As an apparatus for generating plasma, conventional apparatuses utilizing a reactive ion etching system such as a parallel flat plate type or a magnetron type are generally not suitable for obtaining a plasma having the above-mentioned high density. Preferably a helicon wave type and a high-frequency induction type are employed for generating plasma having the above-mentioned high density.

In the dry etching using a gas for plasma reaction of the present invention, the pressure at which the dry etching is carried out is not particularly limited, and usually, the above-mentioned etching gas is introduced in a vacuumed etching apparatus so that the inner pressure thereof reaches a pressure of about 10 to $10^{-5}$ Torr, preferably about $10^{-2}$ to $10^{-3}$ Torr.

The temperature which a substrate to be etched reaches during etching is usually in the range of 0° C. to 300° C., preferably 60° C. to 250° C. and more preferably 80° C. to 200° C. The temperature of substrate may be controlled, for example, by cooling, or may not be controlled. The time for an etching treatment is in the range of about 10 seconds to about 10 minutes. But, a high rate etching can be generally conducted with the gas for plasma reaction of the present invention, and therefore, etching can be conducted within the range of 10 seconds to 3 minutes, which is highly efficient in productivity.

(2) CVD

By the term "CVD" using a gas for plasma reaction of the present invention, as used herein, we mean a technique for activating and polymerizing octafluorocyclopentene by plasma discharge to thereby form a thin polymer film on a substrate to be treated. The process in which the thin polymer film is formed cannot be definitely elucidated, but, it is presumed that octafluorocyclopentene is subjected to ring-opening or additional polymerization as well as decomposition under plasma dissociating conditions. The plasma CVD can be carried out under conditions such as plasma density, varied from those under which the above-mentioned dry etching is conducted, and can also be carried out using a mixture of a gas for plasma reaction of the present invention with another gas.

Articles to be subjected to plasma CVD are not particularly limited. However, plasma CVD is usually applied to a surface of articles and parts to which performances or properties such as electrical insulation, water repellency, anticorrosion, acid resistance, lubricating property and anti-reflection are required in a field of semiconductor production, an electrical or electric field, a precision machinery field or other fields. Preferably it is applied to a surface of articles or parts to which an electrical insulation property is required in a field of semiconductor production or an electrical or electric field.

Plasma CVD is especially suitable for formation of an insulation thin film or an insulation material layer in the production step of a semiconductor device. As specific examples of the thin film formed by plasma CVD, there can be mentioned an inter-laminar insulation thin film on an aluminum metal wiring, and a final passivation film for protecting elements.

As methods for plasma CVD, hitherto known methods can be employed, which include, for example, the method described in Japanese Unexamined Patent Publication No. H9-237783. The plasma generating conditions usually employed are as follows. high-frequency (RF) output power: 10 W to 10 kW, temperature of article to be treated: 0 to 500° C., pressure: 0.1 milli-Torr to 100 Torr. Thickness of the formed thin film is usually in the range of 0.01 to 10 $\mu$m.

As an apparatus used for plasma CVD, a parallel flat-plate type CVD apparatus is generally used. But, a microwave CVD apparatus, an ECR-CVD apparatus and high-density plasma CVD apparatuses including a helicon wave type and a high-frequency induction type can also be used.

Irradiation with ultraviolet, for example, by a low-pressure mercury lamp can be carried out for promoting dissociation of gas for plasma reaction or mitigating a harmful influence on the article to be treated. Irradiation with ultrasonic waves of an article to be treated or a reaction space can also be carried out.

(3) Ashing

By the term "ashing" using a gas for plasma reaction of the present invention, as used herein, we mean a technique for activating octafluorocyclopentene by plasma discharge to thereby ashing and removing contaminant substances present within a chamber of an etching apparatus or a CVD apparatus. The ashing also includes removal of contaminant substances by activated species from a surface of an article to be etched or subjected to CVD, and polishing a surface of an article to be treated whereby the surface is made smooth.

A gas for plasma reaction is especially effectively used for removing an obstructive polymeric ingredient deposited within a chamber of an apparatus, removing an oxide film from a substrate for a semiconductor device, and separating a resist from a semiconductor device. Occurrence of activated species due to plasma decomposition is required for the plasma ashing, and therefore, the conditions for a plasma reaction should be appropriately chosen.

Process for Producing Gas for Plasma Reaction

The process for producing a gas for plasma reaction of the present invention is not particularly limited, but, two processes of the present invention, explained below, are especially preferably employed. The process for synthesizing a crude reaction product predominantly comprised of octafluorocyclopentene (hereinafter abbreviated to "crude reaction product") used in these two processes is not particularly limited.

The process for synthesizing the crude reaction product includes, for example, a process for fluorinating perchlorocyclopentene with potassium fluoride; a process for fluorinating perchlorocyclopentene or perchlorocyclopentadiene with hydrogen fluoride in the presence of a catalyst comprising antimony or chromium as a principal component to give chlorofluorocyclopentene, and then, fluorinating the chlorofluorocyclopentene with potassium fluoride; and a process for dechloro-fluorinating chlorononafluorocyclopentane.

More specifically, of these processes, a process for fluorinating 1-chlorohexafluorocyclopentene with potassium fluoride is preferable. This is because the amount of expensive potassium fluoride can be reduced, and an uneconomical reaction scheme such as introduction of fluorine atoms followed by elimination of the introduced fluorine atoms can be avoided.

The above-mentioned crude reaction product can be obtained usually with a purity of at least 90% by volume. This is because the principal reaction involves substitution of chlorine atoms by fluorine atoms, and thus, the differences in boiling point among a crude reaction product, an intermediate and a raw material are large and the crude reaction product can be easily separated, for example, by fractional distillation. To advantageously carry out the process for producing a gas for plasma reaction of the present invention, the raw material, i.e., the crude reaction product has a purity of at least 95% by volume. The purity is preferably at least 97% by volume, more preferably at least 98% by volume and especially preferably at least 99% by volume.

Impurities contained in the crude reaction product vary depending upon the particular raw material used for the production thereof. The impurities include, for example, 1,2-dichlorohexafluorocyclopentene, 1-chloroheptafluorocyclopentene, chlorononafluorocyclopentane, perfluorocyclopentadiene, perfluorobutadiene, perfluorocyclobutene, perfluorocyclopentane, and oxygen-containing fluoro-five-membered ring compounds with four or five carbon atoms. The production mechanism of the oxygen-containing fluoro-five-membered ring compounds with four or five carbon atoms cannot be definitely elucidated.

The impurities further include nitrogen gas and oxygen gas, which are in a state of dissolved in liquid octafluorocyclopentene by the contact of air or nitrogen gas within a production apparatus with the liquid octafluorocyclopeneten. Further, the impurities include a reaction medium, and moisture derived from moisture-adsorbed potassium fluoride (fluorinating agent).

The process of the present invention for removing the above-mentioned impurities to give a gas for plasma reaction of the present invention includes the following two processes.

The first process is characterized by distilling a crude reaction product predominantly comprised of octafluorocyclopentene in an inert gas of group 0.

The inert gas of group 0 is not particularly limited provided that it falls within group 0 of the periodic table, and it includes, for example, helium, neon, argon, krypton, xenon and radon. Of these, helium, neon and argon are preferable. Helium and argon are more preferable in view of reduced solubility in octafluorocyclopentene and ease in commercial availability. Helium is most preferable. The inert gas of group 0 may be used either alone or as a combination of at least two thereof.

It is essential that fractional distillation is carried out in an inert gas of group 0, but the method of fractional distillation is not particularly limited. The theoretical plate number of a distillation column used is usually at least 30 and preferably at least 50 for effectively removing analogous compounds having a boiling point close to that of octafluorocyclopentene. The pressure at fractional distillation is usually at least −0.5 atm as gauge pressure, and preferably in the range of normal pressure to 10 atm. The reflux ratio is not particularly limited and can be appropriately chosen depending upon the capacity of a distillation column. The reflux ratio is usually at least 2 and preferably at least 5. The fractional distillation may be carried out either in a batchwise or continuous manner. Extractive distillation using an extracting medium can also be conducted.

Drawing of distillates can be effected by controlling temperature of the top of the above-mentioned distillation column. The temperature of the distillation column top may be set approximately the same temperature as the boiling point of a gas for plasma reaction, which varies depending upon the pressure. Moisture contained in a crude reaction product can be azeotropically removed as an initial distillate, and therefore, the moisture content in the main distillates can be reduced to 20 ppm by weight or less. Organic impurities are removed by utilizing the difference in boiling point thereof with octafluoro-cyclopentene.

Nitrogen gas and oxygen gas are removed, for example, by replacing the inner atmosphere of the entire distillation column with an inert gas of group 0 before fractional distillation; prior to drawing of distillates, refluxing the whole ingredients and discontinuing the cooling by a cooling condenser to thereby expel gaseous ingredients dissolved in the charged liquid; or, during fractional distillation, allowing an inert gas of group 0 to flow through a distillation column. The main distillates obtained by fractional distillation are charged in a bomb or other vessel usually in an atmosphere of inert gas of group 0.

The foregoing first production process of the present invention is efficient in that removal of nitrogen gas, oxygen gas, moisture and organic impurities can be simultaneously carried out. By this first production process, a very highly purified gas for plasma reaction can be obtained. More specifically, a high-purity gas for plasma reaction is obtained, which has an octafluorocyclopentene purity of at least 99.9% by volume based on the total volume of the gas for plasma reaction, and wherein the total content of nitrogen gas and oxygen gas, contained as trace gaseous ingredients of the remainder, is not larger than 200 ppm by volume.

A high-purity gas for plasma reaction can also be obtained by the first production process of the present invention, which has an octafluorocyclopentene purity of at least 99.9% by volume based on the total volume of the gas for plasma density, and wherein the total content of nitrogen gas and oxygen gas, contained as trace gaseous ingredients of the remainder, is not larger than 200 ppm by volume, and the content of moisture is not larger than 20 ppm by weight.

The second process of the present invention for producing a gas for plasma reaction is characterized by comprising a first step of distilling a crude reaction product predominantly comprised of octafluorocyclopentene into a purity of at least 99.9% by volume, and a second step of removing trace amounts of impurities of the remainder.

In the first step of the second process of the present invention, it is essential to distillate a crude reaction product to an extent such that the purity of octafluorocyclopentene contained therein is enhanced to at least 99.9% by volume, preferably at least 99.95% by volume and more preferably at least 99.98% by volume.

The method of fractional distillation in the first step is not particularly limited. For example, methods similar to those which are explained above as for the first production process can be employed. However, it is not essential to carry out the fractional distillation in an inert gas of group 0 in the first step, and the fractional distillation in the first step can be carried out, for example, in the co-presence of nitrogen gas because nitrogen gas can be removed in the succeeding second step, mentioned below.

Moisture contained in a crude reaction product can be azeotropically removed as an initial fraction, and therefore, the moisture content in the main fractions can be reduced to 20 ppm by weight or less. The predominant part of organic impurities can be removed by utilizing the difference in boiling point thereof with octafluorocyclopentene, and thus, the purity of octafluorocyclopentene can be enhanced to at least 99.9% by volume. If desired, prior to the fractional distillation in the first step, moisture and organic impurities can be previously removed by using, for example, a desiccant, a molecular sieve or an adsorbent.

By the removal of trace amounts of impurities of the remainder carried out in the second step, we mean usually removal of nitrogen gas and oxygen gas from the product obtained in the first step to an extent such that the total content of nitrogen gas and oxygen gas is not larger than 200 ppm by volume. If desired, an additional step of removing a trace amount of organic impurities, which are not removed by the first step of fractional distillation, can be conducted.

The method of removing trace amounts of impurities of the remainder, more specifically nitrogen gas and oxygen gas, is not particularly limited. But, as preferable examples of the method, there can be mentioned (1) a method of refluxing a product, obtained in the first step, under heating in an inert gas of group 0; (2) a method of conducting a simple distillation in an inert gas of group 0; and (3) a method of placing a product obtained in the first step under a reduced pressure at a low temperature to be thereby degassed. These methods (1), (2) and (3) may be carried out either alone or as a combination of two or more thereof. If desired, prior to or after the methods of (1), (2) and/or (3), an additional method (4) of removing a trace amount of organic impurities by placing a product obtained in the first step in contact with, for example, a molecular sieve or an adsorbent, can be employed.

The above-mentioned methods (1) through (4) will now be more specifically described.

(1) Method of Refluxing with Heating in Inert Gas of Group 0

As mentioned above, octafluorocyclopentene is liquid at normal temperature and readily absorbs air, i.e., nitrogen gas and oxygen gas, to dissolve air therein. Therefore, it is very advantageous that reflux with heating is carried out in an inert gas of group 0 without contact with air to remove nitrogen gas and oxygen gas.

As specific examples of the inert gas of group 0 used for refluxing with heating, there can be mentioned helium, neon and argon. Helium and argon are preferable in view of reduced solubility in octafluorocyclopentene and ease in commercial availability. Helium is most preferable.

The reflux with heating is preferably carried out by a method of previously degassing the whole apparatus and replacing the inner atmosphere with an inert gas of group 0, and, during refluxing, allowing a stream of inert gas or group 0 to flow through the apparatus. Another method can also be employed wherein the reflux with heating is first conducted in a nitrogen gas- or oxygen gas-containing atmosphere to gradually expel the nitrogen gas or oxygen gas by a vapor of octafluorocyclopentene, and then, the apparatus is flushed with an inert gas of group 0 and the reflux with heating is continued in the inert gas atmosphere. The vapor of octafluorocyclopentene generated under heating is cooled by a condenser provided at the top of the apparatus, and liquefied to flow down to a heated vessel provided at a lower part of the apparatus. To prevent discharge of octafluorocyclopentene vapor, a cooling medium in the condenser is maintained usually at a temperature of not higher than 5° C., preferably not higher than 0° C. and more preferably not higher than −20° C.

If nitrogen gas and oxygen gas once removed by refluxing with heating is present in proximity to the liquefying (condensing) part of condenser, it is possible that the nitrogen gas and oxygen gas are again dissolved in the liquid. Therefore, it is recommended that, during reflux in an atmosphere of inert gas of group 0, cooling by the condenser is temporarily stopped to expel a part of the vapor accompanying by nitrogen gas and oxygen gas whereby the entire amount of nitrogen gas and oxygen gas are discharged to the outside.

The pressure at which reflux with heating is conducted may be normal pressure or higher because the boiling point of octafluorocyclopentene is 27° C. But, to efficiently expel the nitrogen gas and oxygen gas, dissolved in the liquid, the reflux is preferably carried out at normal pressure rather than at a high pressure. The heating method may be the same as those which are ordinarily employed for distillation and reaction under heating. Various heating means can be employed, which include, for example, jacket heating, reboiler heating and internal coil heating. The time for reflux with heating is appropriately chosen depending upon the amount of charged material to be refluxed, the amount of reflux and the capacity of a condenser, but, the reflux time is usually at least one hour, preferably at least 3 hours.

(2) Method of Simple Distillation in Inert Gas of Group 0

After continuing the reflux with heating for a determined period of time in an inert gas of group 0, the cooled and condensed liquid can be dispensed to another receptacle without return to the still pot to prevent deterioration due to heating. This system can be said simple distillation conducted in an inert gas of group 0. The operation for single distillation may be the same as that employed in the case where the above-mentioned reflux with heating is carried out. Special apparatus and operations are not necessary.

(3) Method of Placing Product Obtained in First Step Under Reduced Pressure at Low Temperature This method involves a step of placing a distilled product containing nitrogen gas and oxygen gas, obtained in the above-mentioned first step, under a reduced pressure at a low temperature whereby the nitrogen gas and oxygen gas are removed. The operation can be carried out at room temperature or lower. However, when the pressure is reduced at a temperature in the range of room temperature to 0° C., octafluorocyclopentene tends to be volatilized and discharged. Therefore, a temperature below 0° C. is preferable. A temperature below −20° C. is more preferable. A deep cooling trap is preferably equipped in a vacuum line to recover octafluorocyclopentene. The operation pressure is usually in the range of 5 to 200 mmHg, preferably 20 to 50 mmHg.

While the liquid is placed under a reduced pressure, the liquid is preferably shaken or irradiated with ultrasonic waves to enhance the efficiency of degassing.

The longer the time during which the liquid is placed under a reduced pressure, the more enhanced the effect of degassing. But, in view of the loss of octafluorocyclopentene due to evaporation, the liquid is placed under a reduced pressure for a period of 10 seconds to 5 minutes, preferably 30 seconds to 2 minutes. It is also preferable to intermittently place the liquid under a reduced pressure several times. After completion of the vacuuming operation for degassing, the vessel is closed or an inert gas of group 0 is introduced in the vessel until normal pressure is reached whereby the liquid can be prevented from contacting with nitrogen gas and oxygen gas.

(4) Method of Placing in Contact With Molecular Sieve or Adsorbent

This method is advantageously employed in combination with the above-mentioned method (1), (2) or (3) for removing chlorine-containing compounds and oxygen-containing compounds, which are contained in trace amounts in octafluorocyclopentene, to produce a gas for plasma reaction having an ultra-high purity. The oxygen-containing compound includes, for example, compounds which are presumed to have molecular formulae: $C_5F_8O$ and $C_4F_6O$ by gas chromatography mass spectrometric analysis. The chlorine-containing compounds and the oxygen-containing compounds are placed in contact with a molecular sieve or an absorbent such as alumina or active carbon.

The molecular sieve used is not particularly limited. Various kinds of molecular sieves are commercially available, and an appropriate molecular sieve can be chosen therefrom. For example, molecular sieve 3A and 13X (supplied by Wako Pure Chem. Ind., Ltd.) are preferably used. Molecular sieve 13X is especially preferable.

As alumina, lowly crystalline active alumina prepared by heat dehydration of alumina hydrate is preferable, which includes, for example, alumina catalyst N611N supplied by Nikki Chem. Co. As active carbon, there can be mentioned vegetable carbon such as those made from wood, sawdust, charcoal, coconut shell charcoal, palm shell charcoal and charcoal residue of combustion; coal ash such as those made from peat, lignite, brown coal, bituminous coal and anthracite; and petroleum carbon or synthetic resin carbon such as those made from petroleum pitch, acid sludge and oil carbon. Beaded black (granular carbon) (commercially available from, for example, Kishida Chem. Co.) is especially preferable.

By the above-mentioned production process comprising in combination the first step of distilling a crude reaction product predominantly comprised of octafluorocyclopentene into a purity of at least 99.9% by volume, and the second step of removing trace amounts of impurities, such as nitrogen gas and oxygen gas, of the remainder, a high purity gas for plasma reaction can be obtained, which has an octafluorocyclopentene purity of at least 99.9% by volume based on the total volume of the gas for plasma reaction, and wherein the total content of nitrogen gas and oxygen gas, contained as trace gaseous ingredients of the remainder, is not larger than 200 ppm by volume.

A high purity gas for plasma reaction, which has an octafluorocyclopentene purity of at least 99.9% by volume based on the total volume of the gas for plasma reaction, and wherein the total content of nitrogen gas and oxygen gas, contained as trace gaseous ingredients of the remainder, is not larger than 200 ppm by volume, and which has a moisture content of not larger than 20 ppm by weight, can also be obtained.

Further, an ultra-high purity gas for plasma reaction, which has an octafluorocyclopentene purity of at least 99.95% by volume based on the total volume of the gas for plasma reaction, and wherein the total content of nitrogen gas and oxygen gas, contained as trace gaseous ingredients of the remainder, is not larger than 200 ppm by volume, can also be obtained.

Still further, an ultra-high purity gas for plasma reaction, which has an octafluorocyclopentene purity of at least 99.95% by volume based on the total volume of the gas for plasma reaction, and wherein the total content of nitrogen gas and oxygen gas, contained as trace gaseous ingredients of the remainder, is not larger than 200 ppm by volume, and which has a moisture content of not larger than 20 ppm by weight, can also be obtained.

EXAMPLES

The invention will now be described more specifically by the following working examples that by no means limit the scope of the invention.

In these examples, purity (%) of octafluorocyclopentene and contents (ppm) of nitrogen gas and oxygen gas are values as expressed by volume and measured by GC analysis unless otherwise specified. The moisture content (ppm) is a value as expressed by weight and measured by the Karl Fischer Method.

The GC analysis of octafluorocyclopentene was carried out according to the following specifications.

Instrument: HP6890 supplied by Hewlett-Packard Co.

Column: Ultra Alloy +−1(s) (length: 50 m inner diameter: 0.25 mm, membrane thickness: 1.5 μm)

Column temperature: maintained at a constant temperature of 80° C. for 10 minutes, and then, elevated to 200° C. over a period of 20 minutes Injection temperature: 200° C.

Carrier gas: helium (flow rate in volume: 1 ml/min)

Detector: FID

Internal standard substance: n-butane

The GC analysis of oxygen gas and nitrogen gas was carried out according to the following specifications.

Instrument: GC-9A supplied by Shimadzu Corp.

Column: packed column JGC-9A (length: 2 m, inner diameter: 3 mm, column packing: Unibeads C 60/80)

Column temperature: 40° C.

Injection temperature: 150° C.

Carrier gas: helium (flow rate in volume: 50 ml/min)

Detector: TCD

Reference Example 1
(Preparation of Octafluorocyclopentene)

A 200 ml four-necked flask equipped with a dropping funnel, a distillation column, a thermometer and a stirrer was charged under a nitrogen gas stream with 30 g (0.516 mol) of potassium fluoride and 50 ml of N,N-dimethylformamide. A cooling medium maintained at −20° C. was passed through a Dimroth condenser equipped at the top of the distillation column, and a fraction trap equipped in an open line of the distillation column was cooled to −70° C. The dropping funnel was charged with 50.2 g (0.205 mol) of 1,2-dichloro-3,3,4,4,5,5-hexafluorocyclopentene. Temperature of the liquid in the flask was elevated to 135° C. over a period of 0.5 hour.

After commencement of the temperature elevation, the raw material was gradually dropped from the dropping funnel at a rate of 0.07 mol/hour. It was confirmed that temperature of the column top became stable at the boiling point (27° C.) of a reaction product. When 0.7 hour elapsed from the confirmation of the stabilization of temperature (namely, when 1.5 hours elapsed from commencement of the temperature elevation), drawing of fractions was commenced. At an initial stage extending over 3 hours, the fractions were drawn at a rate of 0.07 mol/hour, and the drawing of the fractions was continued until the temperature of the column top commenced to gradually rise from 27° C. (namely, until about 7 hours elapsed from commencement of the initial temperature elevation). Thus, 38.24 g (0.18 mol) of octafluorocyclopentene was obtained. The yield was 87.8% and the purity was 99.82% as measured by GC analysis.

Example 1
(Production of High-Purity Gas for Plasma Reaction)

A one liter round glass flask was charged with 713 g of octafluorocyclopentene having a purity of 99.83%, prepared by the same procedures as described in Reference Example 1, and boiling bubble stone. The flask was equipped with a Sulzerpack distillation column having a theoretical plate number of 55. The charged liquid octafluorocyclopentene contained 436 ppm of nitrogen gas and 71 ppm of oxygen gas.

Helium gas was introduced from the top of condenser of the distillation column at a flow rate of 20 ml/min whereby the atmosphere within the distillation column was replaced with helium. The round flask was dipped in an oil bath, and, while cooling water maintained at 5° C. was circulated through the condenser, the temperature of the content within the flask was elevated to 65° C. and the content was refluxed totally for 1 hour. Thereafter, the circulation of cooling water was stopped, and the vapor of octafluorocyclopentene was allowed to flow upward to the top of condenser and was discharged therefrom for about 3 minutes. Thereafter, the circulation of cooling water was restarted, and the total reflux was continued for 1 hour while helium gas was continuously flowed. At a reflux ratio of 40:1, the fractions were drawn, and collected in a receptacle, the inner atmosphere of which had been previously replaced with helium. Thus, 643 g of octafluorocyclopentene having a purity of 99.98% was obtained. Yield: 90.2%.

The above-mentioned distilled product was filled in a pressure vessel in a manner such that air was not incorporated therein. Samples were taken from the liquid phase and the gas phase. GC analysis of the samples revealed that the contents of oxygen gas and nitrogen gas in the liquid phase were below the limit of detection (i.e., below 10 ppm) and 39 ppm, respectively, and those in the gas phase were 17 ppm and 68 ppm, respectively. The moisture content in the liquid phase as measured by the Karl-Fischer method was 7 ppm by weight.

Comparative Example 1

The operation of fractional distillation described in Example 1 was repeated wherein nitrogen gas was used instead of helium gas with all other conditions remaining the same. Thus, octafluorocyclopentene having a purity of 99.97% was obtained at a distillation yield of about 90%. The octafluorocyclopentene fraction was filled in a pressure vessel, and samples were taken from the liquid phase and the gas phase. GC analysis of the samples revealed that the contents of oxygen gas and nitrogen gas, as measured by GC analysis, in the liquid phase were 15 ppm and 330 ppm, respectively, and the contents of oxygen gas and nitrogen gas in the gas phase were 53 ppm and 538 ppm, respectively.

Reference Example 2
(Preparation of Octafluorocyclopentene)

The same reaction apparatus as used in Reference Example 1 was charged with 36.9 g (0.635 mol) of potassium fluoride and 75 ml of N,N-dimethylformamide. A cooling medium maintained at −10° C. was circulated through a Dimroth condenser equipped at the top of distillation column, and a fraction trap equipped in an open line was cooled to −70° C. The dropping funnel was charged with 51.6 g of a mixture comprising 61.7% of 1,2-dichloro-3,3,4,4,5,5-hexafluorocyclopentene, 30.9% of 1,2,3-trichloro-3,4,4,5,5-pentafluorocyclopentene, 7.1% of 1,2,3,5-tetrachloro-3,4,4,5-tetrafluorocyclopentene and 0.3% of 1,2,3,3,5-pentachloro-4,4,5-trifluorocyclopentene.

The temperature of the liquid in the flask was elevated to 135° C. over a period of 0.5 hour. Thereafter, the raw material was continuously dropped over a period of 3 hours. It was confirmed that temperature of the column top became stable at the boiling point (27° C.) of a reaction product. Then fractions of the reaction product were continuously drawn until the temperature of the column top commenced to rise. Namely, the drawing of the fractions was continued over a period of about 7 hours. The reaction product was taken out and analyzed. Thus, 40.4 g of octafluorocyclopentene was obtained, which had a purity of 99.86% as measured by GC analysis.

Example 2
(Preparation of High-Purity Gas for Plasma Reaction)

First step: Using a distillation column equivalent to that having a theoretical plate number of 55, about 800 g of octafluorocyclopentene having a purity of 99.89%, prepared by the same procedures as described in Reference Example 2, was distilled under a nitrogen gas stream wherein the temperature of column top was 27° C. and the reflux ratio was 40:1. Thus, octafluorocyclopentene having a purity of 99.98% was obtained at a distillation yield of about 90%.

Second step: A one liter round flask equipped with a reflux condenser and a three-way stopcock was charged with 695 g of octafluorocyclopentene, prepared in the above-mentioned first step, and boiling bubble stone. Helium gas was introduced through one passage of the stopcock at a flow rate of 20 ml/min for 3 minutes whereby the atmosphere within the flask and the condenser was replaced with helium. Then the round flask was dipped in a warm water bath maintained at 40° C., and, while helium gas was continuously introduced in the apparatus, octafluorocyclopentene was refluxed with heating. When 20 minutes elapsed, the circulation of cooling water through the condenser was stopped, and the vapor of octafluorocyclopentene was drawn through the three-way stopcock for about one minute. Then, the circulation of cooling water was restarted and a reflux state was restored. When 20 minutes elapsed, the above-mentioned operation was repeated once more, and, when 20 minutes elapsed, the warm water bath was taken off to cool the content to room temperature. Thus, 671 g of octafluorocyclopentene was recovered with a loss of 24 g.

Before and after the reflux was conducted, the contents of nitrogen gas and oxygen gas in the liquid phase and the gas phase were determined by GC analysis. The results are shown in Table 1. After the reflux was conducted, the moisture content in the liquid phase was determined by the Karl-Fischer method. The moisture content was 5 ppm by weight.

TABLE 1

| Analyzed sample | Measured before reflux | | Measured after reflux | |
|---|---|---|---|---|
| | Nitrogen gas content | Oxygen gas content | Nitrogen gas content | Oxygen gas content |
| Liquid phase | 302 | 76 | 23 | Below 10 |
| Gas phase | — | — | 112 | 11 |

(unit: ppm by volume)

Example 3
(Production of High-Purity Gas for Plasma Reaction)

First step: By the same procedures as described in the first step in Example 2, 1.2 kg of octafluorocyclopentene having a purity of 99.98% was obtained.

Second step: While 1 kg of octafluorocyclopentene, obtained in the above-mentioned first step 1, was cooled to 0° C., the octafluorocyclopentene was circulated in a 150 ml Teflon column packed with 100 ml (true volume) of an alumina catalyst N611N (supplied by Nikki Chem. Co.) at a space velocity of 10 (1/hour) by a liquid feed pump. When 5 hours elapsed, the purity of octafluorocyclopentene was analyzed. The purity was 99.99%.

The octafluorocyclopentene was refluxed with heating within an argon gas atmosphere by using the same apparatus and the same procedures as those used in the second step in Example 2. A pressure vessel was charged with the thus-obtained product, and a sample was taken from the liquid phase. Analysis of the sample by the Karl-Fischer method revealed that the moisture content was 4 ppm by weight. Analysis of a sample taken from the gas phase revealed that the content of oxygen gas was lower than the limit of detection, i.e., below 10 ppm, and the content of nitrogen gas was 41 ppm.

Example 4
(Production of High-Purity Gas for Plasma Reaction)

First step: By the same procedures as described in the first step in Example 2, high-purity octafluorocyclopentene was obtained.

Second step: A 200 ml four-necked flask equipped with a helium gas line, a thermometer, a stirrer, a Claisen type simple distillation column, a cooling apparatus and a receptacle was charged with 135 g of octafluorocyclopentene having a purity of 99.98%, and the receptacle was cooled to 0° C. The flask was dipped in a warm water bath maintained at a temperature of 35 to 40° C., and simple distillation was conducted in a helium gas atmosphere. The simple distillation was stopped to obtain 44 g of a distillate and 71 g of a still residue within the flask. The contents of oxygen gas and nitrogen gas in the distillate and the still residue were measured by GC analysis. The results are shown in Table 2. For comparison, the contents of oxygen gas and nitrogen gas in the charged liquid were also similarly measured before the simple distillation. The results are also shown in Table 2.

TABLE 2

| Analyzed liquid | Nitrogen gas content in liquid | Oxygen gas content in liquid |
|---|---|---|
| Liquid charged | 365 | 69 |
| Still residue | 28 | Below 10 |
| Distillate | 13 | Below 10 |

(unit: ppm by volume)

Reference Example 3
(Test for Solubility of Nitrogen Gas in Octafluorocyclopentene)

Each of three 100 ml Kjeldahl flasks was charged in the air with about 50 ml of octafluorocyclopentene having a nitrogen gas content of 70 ppm, prepared by the same procedure as described in Example 1. The three flasks were left to stand at temperatures of −20° C., 0° C. and 20° C., respectively, while the flasks were opened so that the content was in contact with air. 90 minutes later, the content of nitrogen gas in each flask was measured. The contents of nitrogen gas in the three flasks left to stand separately at −20° C. 0° C. and 20° C. were about 2,430 ppm, about 1,930 ppm and about 640 ppm, respectively. These results show that nitrogen gas in the air is rapidly dissolved in octafluorocyclopentene.

Examples 5 to 13

(Dry Etching Using High-Purity Gas for Plasma Reaction)

Three kinds of silicon wafers each having a diameter of 150 mm, on a surface of which a silicon oxide ($SiO_2$) thin film, a photoresist (PR) thin film or a polysilicon (Poly-Si) thin film was formed, were set within a helicon wave-type plasma etching apparatus ("I-4100SH type" made by Anelva Corp.). The inside of the etching apparatus was vacuumed and then the high-purity gas for plasma reaction, prepared in Example 1, was introduced into the etching apparatus at a flow rate of 50 sccm. Etching was conducted under plasma-irradiation conditions with density regions varied by changing the electrical energy for generation of plasma as shown in Table 3, while the pressure inside the etching apparatus was maintained at 5 milli-Torr.

During etching, the temperature of wafers was not controlled, and, in all of the three wafers, the temperature reached about 130° C. The etching times were chosen in the range of 15 to 60 seconds. The etching rate was measured at five points on each wafer, namely, (i) the center, (ii) two points 35 mm apart from the center in opposite directions on a diameter, and (iii) two points 65 mm apart from the center in opposite directions on the diameter. The etching rates measured at the above recited five points on a diameter of the wafer are referred to as etching rate −1, −2, −3, −4 and −5, respectively, in the above-recited order.

The selectivity for etching to photoresist (PR) and that to polysilicon (Poly-Si) were evaluated by comparing the etching rates as measured on silicon oxide ($SiO_2$), photoresist (PR) and polysilicon (Poly-Si) under the same etching conditions, and calculating the selectivity to PR and that to poly-Si according to the following equation, Selectivity=(Average etching rate on $SiO_2$)/(average etching rate on PR or poly-Si)

The etching conditions and the results are shown in Table 3.

TABLE 3

| Example No. | 5 | 6 | 7 | 8 | 9 | 10 | 11 | 12 | 13 |
|---|---|---|---|---|---|---|---|---|---|
| Wafer | SiO$_2$ | PR | Poly-Si | SiO$_2$ | PR | Poly-Si | SiO$_2$ | PR | Poly-Si |
| Power load (W) | 500 | 500 | 500 | 800 | 800 | 800 | 1100 | 1100 | 1100 |
| Plasma density (ions/cm$^3$) | $10^{10-11}$ | $10^{10-11}$ | $10^{10-11}$ | $10^{11}$ | $10^{11}$ | $10^{11}$ | $10^{11-12}$ | $10^{11-12}$ | $10^{11-12}$ |
| Etching time (sec) | 60 | 60 | 15 | 60 | 60 | 15 | 60 | 60 | 15 |
| Etching rate (A/min) | | | | | | | | | |
| Rate-1 | 4822 | 669 | 301 | 6231 | 2495 | 985 | 7056 | 3328 | 1298 |
| Rate-2 | 4993 | 815 | 365 | 6511 | 2489 | 952 | 7036 | 3216 | 1359 |
| Rate-3 | 4983 | 899 | 364 | 6584 | 2548 | 977 | 7185 | 3364 | 1306 |
| Rate-4 | 4732 | 524 | 295 | 6416 | 2490 | 936 | 7062 | 3288 | 1402 |
| Rate-5 | 4415 | 718 | 240 | 5968 | 2488 | 935 | 7031 | 3189 | 1360 |
| Average rate | 4789 | 725 | 313 | 6342 | 2502 | 957 | 7074 | 3277 | 1345 |
| Selectivity to | | | | | | | | | |
| Photoresist | | 6.6 | | | 2.5 | | | 2.2 | |
| Polysilicon | | 15.3 | | | 6.6 | | | 5.3 | |

Comparative Examples 2 to 10

The dry etching procedures employed in Examples 5 to 13 were repeated wherein the high-purity gas for plasma reaction used was substituted by the gas for plasma reaction prepared in Comparative Example 1 with all other conditions remaining the same. The results are shown in Table 4. As seen from Table 4, the selectivities to the materials to be etched were greatly reduced as compared with those obtained in Examples 5 to 13.

TABLE 4

| Comp. Example No. | 2 | 3 | 4 | 5 | 6 | 7 | 8 | 9 | 10 |
|---|---|---|---|---|---|---|---|---|---|
| Wafer | SiO$_2$ | PR | Poly-Si | SiO$_2$ | PR | Poly-Si | SiO$_2$ | PR | Poly-Si |
| Power load (W) | 500 | 500 | 500 | 800 | 800 | 800 | 1100 | 1100 | 1100 |
| Plasma density (ions/cm$^3$) | $10^{10-11}$ | $10^{10-11}$ | $10^{10-11}$ | $10^{11}$ | $10^{11}$ | $10^{11}$ | $10^{11-12}$ | $10^{11-12}$ | $10^{11-12}$ |
| Etching time (sec) | 60 | 60 | 15 | 60 | 60 | 15 | 60 | 60 | 15 |
| Etching rate (A/min) | | | | | | | | | |
| Rate-1 | 4213 | 2431 | 1396 | 5911 | 4156 | 2156 | 6565 | 5556 | 2543 |
| Rate-2 | 4057 | 2351 | 1269 | 5812 | 4106 | 2389 | 6713 | 5541 | 2679 |
| Rate-3 | 4187 | 2268 | 1423 | 5749 | 4219 | 2154 | 6698 | 5597 | 2796 |
| Rate-4 | 4256 | 2344 | 1358 | 5865 | 4098 | 2210 | 6683 | 5655 | 2816 |
| Rate-5 | 4152 | 2156 | 1254 | 5898 | 4136 | 2296 | 6801 | 5591 | 2538 |
| Average rate | 4173 | 2310 | 1340 | 5847 | 4143 | 2241 | 6692 | 5588 | 2674 |
| Selectivity to | | | | | | | | | |
| Photoresist | | 1.8 | | | 1.4 | | | 1.2 | |
| Polysilicon | | 3.1 | | | 2.6 | | | 2.5 | |

Example 14
(Formation of CVD Insulation Film Using High-Purity Gas for Plasma Reaction)

Plasma CVD was carried out on an insulation film by using the high-impurity gas for plasma reaction prepared in Example 2. In CVD, a wafer of partially aluminum-deposited silicon oxide film was used as a substrate, and a parallel flat-plate type plasma CVD apparatus was used as a plasma CVD apparatus. The CVD was conducted under the following conditions.
  Flow rate of high-purity gas for plasma reaction: 40 sccm
  Flow rate of argon: 400 sccm
  Pressure: 250 milli-Torr
  RF output power: 400 W at a frequency of 13.56 MHz
  Substrate temperature: 260° C.
By conducting CVD under the above-specified conditions, a thin film having a thickness of 0.5 μm was formed on the substrate. The thin film had no void and was highly dense, and uniform. Adhesion of the thin film to the substrate was good. The thin film had a dielectric constant of 2.4.

Comparative Example 11

The procedures employed in Example 14 were repeated wherein the gas for plasma reaction prepared in Comparative Example 1 was used instead of the high-purity gas for plasma reaction with all other conditions remaining the same. Thus, a thin film having a thickness of about 0.4 μm was formed, which had voids on the surface and was not uniform.

INDUSTRIAL APPLICABILITY

The gas for plasma reaction of the present invention comprised of octafluorocyclopentene has very high purity and uniformity as seen from the above mentioned working examples.

Therefore, plasma reaction as involved, for example, in plasma etching, plasma CVD and plasma ashing can be carried out with high precision and reproducibility. The present invention can respond to requirements such as production of highly integrated, densified and large-sized semiconductor devices.

What is claimed is:

1. A gas for plasma reaction, consisting of: octafluorocyclopentene having a purity of at least 99.9% by volume; and no more than 0.1% trace gaseous impurities, wherein a total content of nitrogen gas and oxygen gas contained in said trace gaseous impurities, is not larger than 150 ppm by volume.

2. The gas for plasma reaction according to claim 1 wherein said gas has a moisture content of not larger than 20 ppm by weight.

3. The gas for plasma reaction according to claim 1 wherein said gas is used for dry etching, chemical vapor deposition or ashing.

4. The gas for plasma reaction according to claim 1, wherein the octafluorocyclopentene has a purity of at least 99.95% by volume.

5. The gas for plasma reaction according to claim 1, wherein the octafluorocyclopentene has a purity of at least 99.98% by volume.

6. The gas for plasma reaction according to claim 1, wherein the total content of nitrogen gas and oxygen gas is not larger than 100 ppm by volume.

* * * * *